United States Patent
Huang et al.

(10) Patent No.: US 10,463,605 B2
(45) Date of Patent: Nov. 5, 2019

(54) CAMELLIA EXTRACT, ITS PREPARATION METHOD, AND ITS USE

(71) Applicant: SHANGHAI DEGAO INDUSTRY CO., LTD., Shanghai (CN)

(72) Inventors: Yongqian Huang, Shanghai (CN); Zhen Yang, Shanghai (CN)

(73) Assignee: SHANGHAI DEGAO INDUSTRY CO., LTD., Shanghai (CN)

( * ) Notice: Subject to any disclaimer, the term of this patent is extended or adjusted under 35 U.S.C. 154(b) by 46 days.

(21) Appl. No.: 16/060,513

(22) PCT Filed: Jul. 17, 2017

(86) PCT No.: PCT/CN2017/093117
§ 371 (c)(1),
(2) Date: Jun. 8, 2018

(87) PCT Pub. No.: WO2018/019145
PCT Pub. Date: Feb. 1, 2018

(65) Prior Publication Data
US 2018/0353424 A1 Dec. 13, 2018

(30) Foreign Application Priority Data
Jul. 25, 2016 (CN) .......................... 2016 1 0589483

(51) Int. Cl.
*A61K 36/82* (2006.01)
*A61K 8/9789* (2017.01)
*A61Q 19/02* (2006.01)
*A61Q 19/08* (2006.01)

(52) U.S. Cl.
CPC ............ *A61K 8/9789* (2017.08); *A61Q 19/02* (2013.01); *A61Q 19/08* (2013.01); *A61K 2800/82* (2013.01)

(58) Field of Classification Search
CPC ....................................................... A61K 36/82
See application file for complete search history.

(56) References Cited

FOREIGN PATENT DOCUMENTS

| CN | 103897429 A | 7/2014 |
| CN | 105997754 A | 10/2016 |
| KR | 20120049459 A | 5/2012 |
| WO | WO-2016016515 A1 | 2/2016 |

OTHER PUBLICATIONS

Azuma et al., Flavonoids and fatty acids of Camellia japonica leaves extract, Revista Brasileira de Farmacognosia Brazilian Journal of Pharmacognosy, vol. 21, No. 6, Jul. 29, 2011, pp. 1159-1162.

*Primary Examiner* — Rosanne Kosson
(74) *Attorney, Agent, or Firm* — Rabin & Berdo, P.C.

(57) ABSTRACT

A preparation method for *camellia* extract includes the following steps: 1) Removing impurities from fresh *camellia* and/or fresh *camellia* buds, cutting the fresh *camellia* and/or fresh *camellia* buds into small sections for use as raw materials; 2) Placing a certain quantity of raw materials into a ultrasonic vessel, adding in a solvent having a mass ratio of 1:3 to 1:30 to form a mixture, uniformly stirring the mixture, and then adding in a certain amount of inorganic acid and/or organic acid to adjust the pH value to 1.3 to 3.0, then soaking the raw materials for 10 minutes to 30 minutes; 3) Performing ultrasonic treatment for 30 minutes to 60 minutes, controlling the ultrasonic frequency to be 20 KHz to 25 KHz, the ultrasonic power to be 1000 W to 2000 W, the ultrasonic temperature to be 15° C. to 50° C., then performing filtration, sterilization and detection to obtain *camellia* extract.

13 Claims, 4 Drawing Sheets

CAMELLIA EXTRACT, ITS PREPARATION METHOD, AND ITS USE

TECHNICAL FIELD

The subject of the present invention belongs to the field of cosmetics. In particular, it is about a *camellia* extract, its preparation method, and its use.

BACKGROUND

*Camellia* belongs to the *camellia* of theaceae. It originated from China, and it has a long history of cultivation. Nowadays, countries such as Japan, South Korea, Australia and the United States have developed rapidly in breeding, planting and production of *camellia*, and have entered into the stage of industrialization. *Camellia* has the function of activating blood circulation and arresting bleeding, reducing diarrhea and reducing the acne. Furthermore, *camellia* is rich in antioxidants such as flavonoids, saponins, and polyphenols, and has amazing effect of anti-aging and anti free-radical. Cosmetics with *camellia* extract as active ingredient have functions like anti free-radical, anti-aging, making spots fade away, moisturising and sun-blocking.

Currently, the most popular methods to prepare *camellia* extract are: 1) heat reflux extraction or distillation by using organic solvent; 2) extraction at a high temperature by using water as the solvent. However, *camellia* extract prepared by these methods has low content of anti-oxidation active ingredients. For the convenience of storage, concentrating the *camellia* extract into *camellia* concentrate or making the *camellia* extract into *camellia* powder is required. When you need *camellia* extract, you can dilute or dissolve the *camellia* concentrate or powder. However, the active ingredients in such *camellia* concentrate or powder declined, leading to the loss of the natural color and fragrance of *camellia* flower, and the effects of anti-oxidation and anti free-radical greatly decreased.

So, it is of great significance to invent a method to prepare *camellia* extract which has high content of anti-oxidation ingredients, good security and high stability.

SUMMARY

The first object of the present invention is to provide a preparation method for *camellia* extract so as to overcome the deficiencies of the current technology. The *camellia* extract has high content of anti-oxidation ingredients, excellent anti-oxidation function, good safety and high stability.

To achieve the above object, the technical solution of the present invention is as follows:

A preparation method for *camellia* extract, comprising the following steps:

1) Removing impurities from fresh *camellia* and/or fresh *camellia* buds, cutting the fresh *camellia* and/or fresh *camellia* buds into small sections for use as raw materials;

2) Placing a certain quantity of raw materials into a ultrasonic vessel, adding in a solvent having a mass ratio of 1:3 to 1:30 to form a mixture, uniformly stirring the mixture, and then adding in a certain amount of inorganic acid and/or organic acid to adjust the pH value to 1.3 to 3.0, then soaking the raw materials for 10 minutes to 30 minutes;

3) Performing ultrasonic treatment for 30 minutes to 60 minutes, controlling the ultrasonic frequency to be 20 KHz to 25 KHz, the ultrasonic power to be 1000 W to 2000 W, the ultrasonic temperature to be 15° C. to 50° C., then performing filtration, sterilization and detection to obtain *camellia* extract.

Further, the length of small sections in step 1) is 0.5 cm to 3 cm.

Further, the mass ratio between the acid and the solvent in step 2) is 0.25% to 2.5%, the acid chosen from inorganic acid, organic acid, and mixtures thereof.

Further, alternatively, the solvent in step 2) chosen from water, ethanol, 1,3-propanediol, 1,2-propanediol, glycerin, 1,3-butanediol, sorbitol, and mixtures thereof.

Further, the inorganic acid in step 2) chosen from hydrochloric acid, acetic acid and mixtures thereof.

Further, the organic acid in step 2) chosen from phytic acid, citric acid, ascorbic acid, lactic acid and mixtures thereof.

According to the second object of the present invention, the *camellia* extract prepared by the method as defined above is provided.

Further, the *camellia* extract contains antioxidant ingredients as follows: kaempferol: 0.43-4.52 ppm, quercetin: 1.09-8.17 ppm, quercitrin: 45.62-197.81 ppm.

According to the third object of the present invention, use of the *camellia* extract as defined above as the active ingredient using in the preparation of cosmetics.

Further, use of the *camellia* extract as defined above as the active ingredient using in the preparation of cosmetics with antioxidant property.

The present invention also provides a whitening toner containing the *camellia* extract as defined above as active ingredient, the whitening toner is composed of the following components by weight percentages:

*camellia* extract 2.0%~10.0%, botanical soothing agent 1.0%~3.0%, glycerin 2.0%~5.0%, 1,3-butanediol 2.0%~6.0%, trehalose 0.2%~5.0%, betaine 0.2%~2.0%, tremella fuciformis polysaccharide 0.005%~0.4%, sodium hyaluronate 0.005%~0.2%, phenoxyethanol 0.3%~0.6%, ethylhexylglycerin 0.1%~0.3%, essential oils 0.1%~0.3%, the rest is water.

The present invention also provides an anti-aging whitening gel containing the *camellia* extract as defined above as active ingredient, the anti-aging whitening gel is composed of the following components by weight percentages:

*camellia* extract 1.0%~10.0%, botanical soothing agent 1.0%~3.0%, glycerin 2.0%~6.0%, 1,3-propanediol 2.0%~6.0%, trehalose 0.2%~5.0%, betaine 0.2%~2.0%, sodium hyaluronate 0.005%~0.2%, xanthan gum 0.5%~1.0%, disodium EDTA 0.05%~0.20%, phenoxyethanol 0.3%~0.6%, ethylhexylglycerin 0.1%~0.3%, essential oils 0.1%~0.3%, the rest is water.

The present invention also provides an anti-aging whitening lotion containing the *camellia* extract as defined above as active ingredient, the anti-aging whitening lotion is composed of the following components by weight percentages:

*camellia* extract 1.0%~8.0%, grape seed oil 5.0%~11.0%, olive oil 7.0%~12.0%, glycerin 2.0%~6.0%, 1,3-propanediol 2.0%~6.0%, caprylic/capric triglyceride 1.5%~4.0%, *glycine soja* (soybean) seed extract 0.5%~1.0%, carbomer 0.2%~0.8%, sodium hyaluronate 0.005%~0.1%, phenoxyethanol 0.3%~0.6%, ethylhexylglycerin 0.1%~0.3%, essential oils 0.1%~0.3%, sodium hydroxide (33 wt %) 0.2%~0.8%, the rest is water.

The present invention also provides an antioxidant whitening sleep mask containing the *camellia* extract as defined above as active ingredient, the antioxidant whitening sleep mask is composed of the following components by weight percentages:

*camellia* extract 2.0%~15.0%, glycerin 1.0%~4.0%, 1,3-propanediol 2.0%~6.0%, 1,3-butanediol 2.0% 6.0%, trehalose 0.5% 2.0%, tremella fuciformis polysaccharide 0.005%~0.3%, ammonium acryloyldimethyltaurate/VP copolymer 0.4%~0.9%, sodium hyaluronate 0.005%~0.2%, disodium EDTA 0.05%~0.2%, phenoxyethanol 0.3%~0.6%, ethylhexylglycerin 0.1%~0.3%, essential oils 0.1%~0.3%, the rest is water.

The present invention also provides an antioxidant whitening cream containing the *camellia* extract as defined above as active ingredient, the antioxidant whitening cream is composed of the following components by weight percentages:

*camellia* extract 2.0%~6.0%, jojoba oil 5.0%~12.0%, shea butter 4.0%~8.0%, cetearyl glucoside 2.5%~6.0%, olive oil 1.0%~5.0%, wheat germ oil 2.0%~5.0%, glycerin 2.0% 5.0%, 1,3-propanediol 2.0% 6.0%, caprylic/capric triglyceride 1.0% 5.0%, trehalose 0.5%~4.0%, *glycine soja* (soybean) seed extract 0.5%~1.0%, tocopheryl acetate 0.05%~0.5%, sodium hyaluronate 0.005%~0.1%, tremella fuciformis polysaccharide 0.005%~0.2%, phenoxyethanol 0.3%~0.6%, ethylhexylglycerin 0.1%~0.3%, essential oils 0.1%~0.3%, the rest is water.

Compared with the current technology, the present invention has the following beneficial effects:

1) The *camellia* extract obtainable by the method as defined above is full of effective antioxidant ingredients, and is rich in low stability-antioxidant ingredients, pigment and volatile oil. Moreover, the extract can keep stability by that method. Because the *camellia* extract keeps the color, fragrance and the active ingredients of fresh *camellia* flower and/or fresh *camellia* flower bud to the maximum, the *camellia* extract has excellent anti-oxidation function, good safety and high stability.

2) Cosmetics containing the *camellia* extract as active ingredient are safe, such cosmetics have no side effects, they could promote cell metabolism effectively, maintain skin elasticity, improve skin nutrition, and they have excellent effects such as whitening, removing beverage, anti-aging effect. The cosmetics could effectively postpone the aging of the skin, make the skin reappear luster and elasticity.

DETAILED DESCRIPTION

Figure 1:
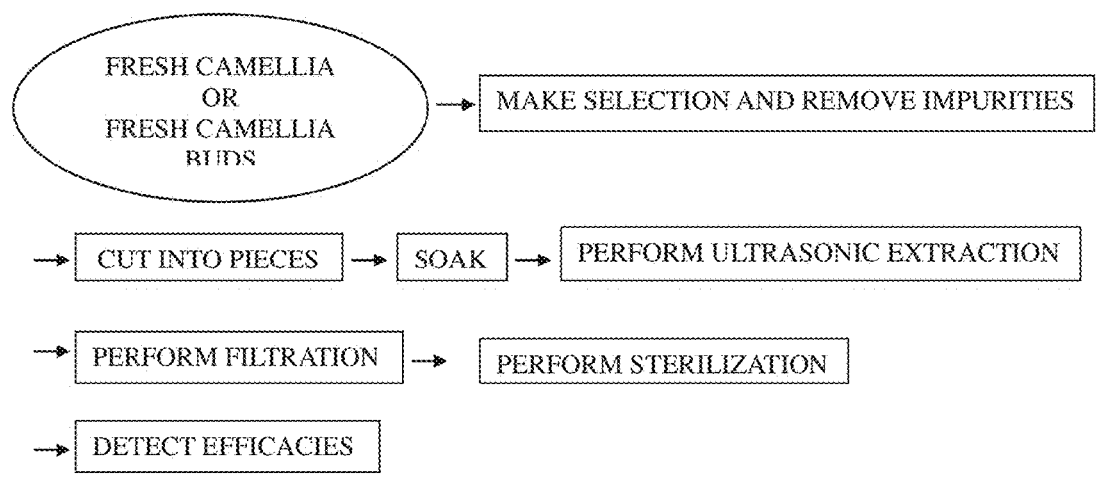
FIG. 1 is a process flow diagram of the preparation of *camellia* extract of the present invention.

The present invention is described in greater detail below with reference to several exemplary embodiments. It is easy to be understood that the detailed embodiments set forth are just for the purpose of illustrating the invention rather than limiting its scope.

Raw materials and apparatus of the present invention are commercially available.

Test Method for Efficacy:

(1) The DPPH Radical Scavenging Test

The analysis method of DPPH (1, 1-diphenyl-2-trinitrophenylhydrazine) is based on that the DPPH radical has a single electron, and it can be monitored as an ingredient in a chemical reaction which containing free radicals. Therefore, it is used to evaluate the antioxidant capacity in vitro.

(2) The ABTS Radical Scavenging Test

The analysis method of ABTS (2,2'-Azino-di-(3-ethyl-benzthiazoline-6-sulfonic acid) is based on that the ABTS radical can be oxidized to green ABTS■+ by appropriate oxidant, and the generation of ABTS■+ is inhibited in the presence of antioxidants. The total antioxidant capacity of the sample can be calculated by measuring ABTS absorbance at 734 nm or 405 nm. ABTS is widely applied in the measurement of the total antioxidant capacity of the natural water-soluble phenolic compounds.

(3) The Quantitative Analysis Experiment of HPLC

HPLC conditions: shimadzu C18 reverse phase column, using methanol-0.4% phosphoric acid as the mobile phase, mobile phase flow rate: 1.0 mL·min$^{-1}$, detection wavelength: 370 nm, column temperature: 40° C., injection volume: 10 μL.

Commercially available samples (quercetin (AR, 99.9%), kaempferol (AR, 99.9%), quercetin (AR, 99.9%)) are used as standard samples to analyze the content of quercetin, kaempferol and quercetin in the *camellia* extract.

(4) Safety Test

10% *camellia* extract diluent was used to perform patch test. The 10% *camellia* extract diluent was prepared by adding 10 g *camellia* extract into 90 g water.

Place 4 pieces of gauze in size of 1 cm$^2$ into the diluents to soak, then put the gauze on the forearm flexor side, then cover with transparent cellophane which is slightly larger than the gauze, and fix by plaster. After 48 hours, remove the gauze and examine the skin reaction, then judge the *camellia* extract safety results according to the grading standards of the skin reactions after 48 and 72 hours.

(5) Stability Test

According to stability test method, the *camellia* extract is stored at the following conditions for 1-3 months respectively: 50° C., 4° C. (refrigerator conditions), room temperature (25° C.), direct sunlight. By observing the change of the color, the DPPH radical scavenging test, and the ABTS radical scavenging test to judge the stability of the *camellia* extract.

(6) Performance Evaluation of Cosmetics

Use Skin test instrument from the Courage+Khazaka electronic GmbH (CK) for the skin tests. The change of the pigments at the skin can be obtained by infrared photography, and further the date of skin wrinkles and skin appearance is obtainable.

EXAMPLE 1~11

The Preparation of the *Camellia* Extract

The method to prepare *camellia* extract, comprising the following steps:

1) Removing impurities from fresh *camellia* and/or fresh *camellia* buds, then cutting the fresh *camellia* and/or fresh

*camellia* buds into small sections for use as raw materials; the length of the small sections is 0.5 cm to 3 cm;

2) Placing a certain quantity of raw materials into a ultrasonic vessel, and adding in the solvent to form a mixture, the mass ratio between the raw materials and the solvent is 1:3 to 1:30, uniformly stirring the mixture, and then adding in a certain amount of inorganic acid and/or organic acid to adjust the pH value to 1.3 to 3.0, then soaking the raw materials for 10 minutes to 30 minutes;

3) After soaking, performing ultrasonic treatment for the mixture in step 2) for 30 minutes to 60 minutes, controlling the ultrasonic frequency to be 20 KHz to 25 KHz, the ultrasonic power to be 1000 W to 2000 W, the ultrasonic temperature to be 15° C. to 50° C., then performing filtration, sterilization to obtain *camellia* extract.

4) Performing efficacy detection of the *camellia* extract obtained by step 3).

*Camellia* extract formulations of Example 1 to 11 are shown in Table 1.

COMPARATIVE EXAMPLE 1~2

Two commercially available *camellia* extract were adopted for the comparison, and the efficacy of the two commercially available *camellia* extract were tested. The two commercial *camellia* extracts were obtained by heating with the ethanol extraction.

EXAMPLE 12

Figure 2:
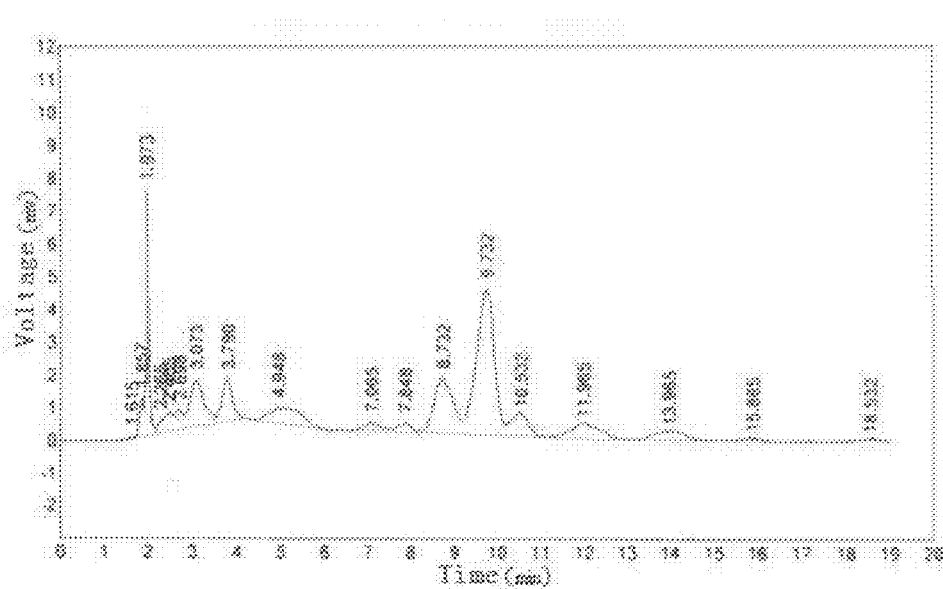
FIG. 2 is a HPLC chromatograms of the *camellia* extract prepared by Example 3 of the present invention.
Figure 3:
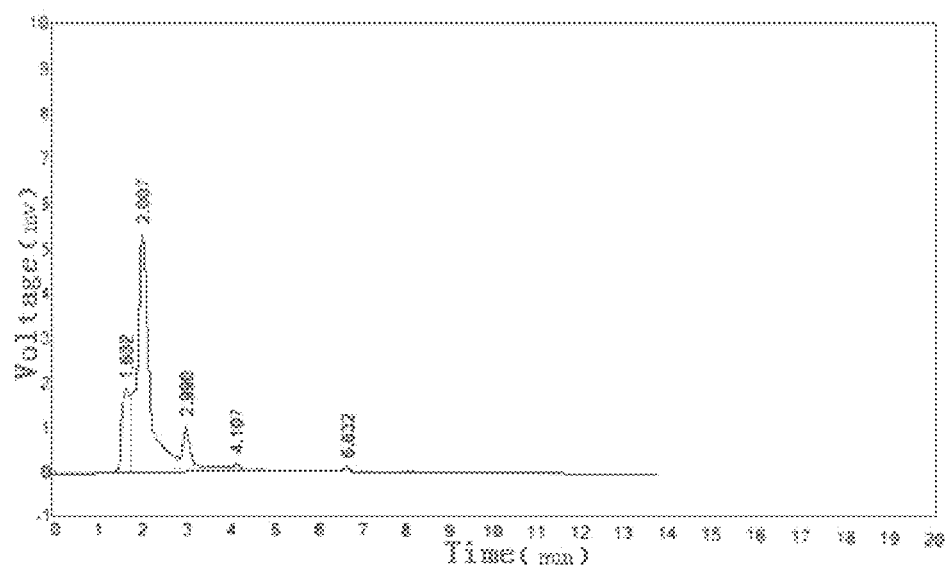
FIG. 3 is a HPLC chromatograms of the *camellia* extract prepared by comparative Example 1 of the present invention.
Figure 4:
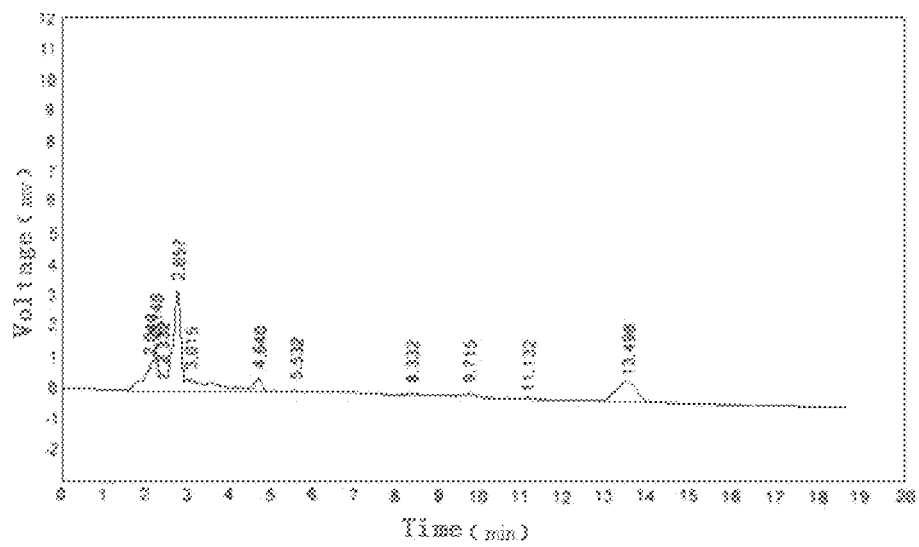
FIG. 4 is a HPLC chromatograms of the *camellia* extract prepared by comparative Example 2 of the present invention.

The active ingredients of the *camellia* extract from Example 1-11 and the comparative Example 1-2 were tested by the HPLC, the HPLC chromatograms of the *camellia* extract of Example 3, comparative Example 1 and comparative Example 2 were shown as FIG. 2, FIG. 3 and FIG. 4. From FIG. 2 to FIG. 4, we could conclude that the *camellia* extract of the present invention contains a variety of active ingredients, and the kinds and the content of the active ingredients were significantly higher than the *camellia* extract of comparative Example 1-2.

The content of antioxidant active ingredients of the *camellia* extract from Example 1-11, and comparative Example 1-2 were shown in Table 2 and Table 3.

TABLE 1

The *camellia* extract formulations

| | raw materials | Example 1 | Example 2 | Example 3 | Example 4 | Example 5 | Example 6 | Example 7 | Example 8 | Example 9 | Example 10 | Example 11 |
|---|---|---|---|---|---|---|---|---|---|---|---|---|
| | | | | | | mass (kg) | | | | | | |
| | *Camellia* | 7.2 | — | 14.4 | 7.2 | — | 7.2 | 7.2 | 7.2 | — | 7.2 | — |
| | *Camellia* bud | — | 7.2 | — | — | 7.2 | — | — | — | 7.2 | — | 7.2 |
| Solvent | Deionized water | 90 | 90 | 45 | 90 | 90 | 45 | 90 | 100 | 100 | 21.6 | 100 |
| | Ethanol | — | — | 45 | — | — | — | — | — | — | — | 100 |
| | 1,2-propanediol | — | — | — | — | — | 45 | — | — | — | — | — |
| | 1,3-propanediol | — | — | — | — | — | 14.4 | 14.4 | 14.4 | — | — | 16 |
| | glycerin | — | — | — | — | — | 30 | — | 30 | — | — | — |
| | 1,3-butanediol | — | — | — | — | — | — | 30 | — | 30 | — | — |
| | Sorbitol | — | — | — | — | — | — | — | — | 14.4 | — | — |
| Acid | Phytic acid (70%) | — | — | — | 0.9 | 0.8 | — | — | — | 0.9 | — | 0.8 |
| | Citric acid (50%) | 0.9 | — | 0.9 | — | — | — | 0.9 | — | — | — | — |
| | Ascorbic acid (50%) | 0.9 | — | — | 0.9 | — | — | — | — | — | 0.54 | — |
| | Lactate (99%) | — | — | — | — | — | — | — | — | 0.9 | — | — |
| | hydrochloric acid (33%) | — | 0.6 | — | — | — | — | — | 0.2 | 0.3 | — | — |
| | Acetic acid (99.5%) | — | — | — | — | — | — | — | 0.161 | — | — | — |
| pH of Soaking solution | | 1.8 | 1.3 | 2.0 | 2.0 | 1.6 | 1.7 | 3.0 | 2.5 | 1.6 | 1.5 | 2.5 |
| Operating parameters | | | | | | | | | | | | |
| Soaking time (min) | | 10 | 15 | 30 | 15 | 25 | 25 | 30 | 25 | 25 | 10 | 30 |
| Ultrasonic frequency (KHz) | | 20 | 22 | 23 | 24 | 25 | 20 | 25 | 22 | 25 | 22 | 25 |
| Ultrasonic power (KW) | | 1.5 | 1.2 | 2.0 | 1.0 | 1.0 | 1.5 | 1.5 | 1.5 | 1.5 | 1.0 | 1.5 |
| Ultrasonic time (min) | | 30 | 30 | 50 | 30 | 30 | 50 | 60 | 50 | 50 | 30 | 40 |
| Ultrasonic temperature (° C.) | | 25 | 35 | 35 | 25 | 25 | 30 | 30 | 30 | 30 | 15 | 50 |

Note:
the concentration of acid is mass concentration in table 1

TABLE 2

Content of the antioxidant active ingredients of the *camellia* extract obtained from Examples 1-11

| The antioxidant active ingredient | Example 1 | Example 2 | Example 3 | Example 4 | Example 5 | Example 6 | Example 7 | Example 8 | Example 9 | Example 10 | Example 11 |
|---|---|---|---|---|---|---|---|---|---|---|---|
| | | | | | Content (ppm) | | | | | | |
| Kaempferol | 0.75 | 0.85 | 1.55 | 0.95 | 1.03 | 1.23 | 1.15 | 0.79 | 0.86 | 4.52 | 0.43 |
| Quercetin | 1.69 | 1.97 | 3.62 | 2.51 | 3.91 | 3.24 | 2.96 | 1.76 | 1.85 | 8.17 | 1.09 |
| Quercitrin | 70.14 | 75.33 | 97.54 | 86.36 | 106.36 | 96.32 | 100.36 | 73.6 | 77.63 | 197.81 | 45.62 |

TABLE 3

Content of the antioxidant active ingredients of the *camellia* extract from comparative Example 1-2

| The content of antioxidant active ingredient (ppm) | comparative Example 1 | comparative Example 2 |
|---|---|---|
| Kaempferol | 0 | 0.25 |
| Quercetin | 0.63 | 1.2 |
| Quercitrin | 0 | 65.0 |

According to the data in Table 2 and Table 3, the *camellia* extract of comparative Example 1 only has one kind of antioxidant ingredient: quercetin; Though the *camellia* extract of comparative Example 2 has three kinds of antioxidant ingredients: kaempferol, quercetin and quercitrin, but the content of antioxidant ingredients of the *camellia* extract obtained from Examples 1 to 11 were significantly higher than that of comparative Example 1-2. It can be concluded that the kinds of antioxidant ingredients are much comprehensive than that of the comparative Example 1-2, and the content of antioxidant ingredients of the *camellia* extract of the present invention is higher than that of the comparative Example 1-2.

EXAMPLE 13

The DPPH Radical Scavenging Test

Weigh 0.04 g, 0.08 g, 0.16 g, 0.312 g, 0.625 g, 1.25 g, 2.5 g, 5.0 g and 10.0 g *camellia* extract prepared by Example 1, and then add water to reach 100 g respectively to form detection solutions, so the concentration of the detection solutions were 0.04%, 0.08%, 0.16%, 0.312%, 0.625%, 1.25%, 2.5%, 5.0% and 10.0% respectively. Then test the detection solution by DPPH radical scavenging test, the results are as follows:

TABLE 4

The DPPH radical scavenging rate of different concentrations of detection solutions

| Test Project | concentration of detection solution (%) | | | | | | | | | |
|---|---|---|---|---|---|---|---|---|---|---|
| | 0 | 0.04 | 0.08 | 0.16 | 0.312 | 0.625 | 1.25 | 2.5 | 5.0 | 10.0 |
| The DPPH radical scavenging rate (%) | 0 | 2.5 | 7.0 | 15.2 | 38.7 | 63.3 | 80.8 | 94.8 | 95.0 | 95.1 |

According to the data in Table 4, we can conclude that the DPPH radical scavenging rate increased with the increasing of the concentration of the detection solution. When the concentration of detection solution is greater than 2.5%, the DPPH radical scavenging rate tends to be stable. It says that the detection solution has good oxidation resistance when the concentration reaches 2.5%.

*Camellia* extracts from Example 1 to 11, and comparative Example 1-2 were used to prepare detection solution at the concentration of 2.5%. Then test the detection solutions by DPPH radical scavenging test, the results are as follows:

TABLE 5

The DPPH radical scavenging rate of detection solutions containing *camellia* extract of Example 1 to 11

| Test Project | Example 1 | Example 2 | Example 3 | Example 4 | Example 5 | Example 6 | Example 7 | Example 8 | Example 9 | Example 10 | Example 11 |
|---|---|---|---|---|---|---|---|---|---|---|---|
| The DPPH radical scavenging rate (%) | 94.8 | 95.7 | 96.8 | 95.6 | 97.87 | 96.0 | 95.8 | 92.8 | 93.5 | 99.7 | 85.4 |

TABLE 6

The DPPH radical scavenging rate of detection solutions containing *camellia* extract of comparative Example 1-2

| Test Project | comparative Example 1 | comparative Example 2 |
|---|---|---|
| The DPPH radical scavenging rate (%) | 50.6 | 48.4 |

According to the data in Table 5 and Table 6, it can be seen that The DPPH radical scavenging rate of detection solutions containing *camellia* extract from Example 1 to 11 are significantly higher than that of the comparative Example 1-2 under the same concentration of detection solution. The DPPH radical scavenging rate of *camellia* extracts from Example 1 to 11 are almost twice of the comparative Example 1-2, which says that the *camellia* extract of the present invention has excellent antioxidant properties.

EXAMPLE 14

The ABTS Radical Scavenging Test

Weigh 0.04 g, 0.08 g, 0.16 g, 0.312 g, 0.625 g, 1.25 g, 2.5 g, 5.0 g and 10.0 g *camellia* extract prepared by Example 1, and then add water to reach 100 g respectively to form detection solutions, so the concentration of the detection solutions were 0.04%, 0.08%, 0.16%, 0.312%, 0.625%, 1.25%, 2.5%, 5.0% and 10.0% respectively. Then test the detection solution by ABTS radical scavenging test, the results are as follows:

TABLE 7

The ABTS radical scavenging rate of different concentrations of detection solution

| Test Project | The concentrations of detection solution (%) | | | | | | | | | |
|---|---|---|---|---|---|---|---|---|---|---|
| | 0 | 0.04 | 0.08 | 0.16 | 0.312 | 0.625 | 1.25 | 2.5 | 5.0 | 10.0 |
| The ABTS radical scavenging rate (%) | 0 | 20.0 | 32.0 | 43.5 | 63.3 | 73.6 | 80.8 | 96.1 | 96.8 | 97.6 |

According to the data in Table 7, we can conclude that the ABTS radical scavenging rate increased with the increasing of the concentration of the detection solution. When the concentration of detection solution is greater than 2.5%, the ABTS radical scavenging rate tends to be stable. It says that the detection solution has good oxidation resistance when the concentration reaches 2.5%.

*Camellia* extracts from Example 1 to 11 and comparative Example 1-2 were used to prepare detection solutions at the concentration of 2.5%. Then test the detection solutions by ABTS radical scavenging test, the results are as follows:

TABLE 8

The ABTS radical scavenging rate of detection solutions containing *camellia* extracts of Example 1 to 11

| Test Project | Example 1 | Example 2 | Example 3 | Example 4 | Example 5 | Example 6 | Example 7 | Example 8 | Example 9 | Example 10 | Example 11 |
|---|---|---|---|---|---|---|---|---|---|---|---|
| The ABTS radical scavenging rate (%) | 93.5 | 94.7 | 96.2 | 94.4 | 96.1 | 94.6 | 95.8 | 95.1 | 94.3 | 98.9 | 82.9 |

TABLE 9

The ABTS radical scavenging rate of detection solutions containing *camellia* extracts of comparative Example 1-2

| Test Project | comparative Example 1 | comparative Example 2 |
|---|---|---|
| The ABTS radical scavenging rate (%) | 62.4 | 59.6 |

According to the data in Table 8 and Table 9, it can be seen that The ABTS radical scavenging rate of detection solutions containing *camellia* extracts of Example 1 to 11 are significantly higher than that of the comparative Example 1-2 under the same concentration of detection solution, which says that the *camellia* extract of the present invention has excellent antioxidant properties.

EXAMPLE 15

Safety Test

In order to confer the safety of the *camellia* extract of the present invention, *camellia* extracts from Example 1 to 11 were tested according to safety test method (patch test). The grading standards of the skin reactions of the patch test were shown in table 10.

TABLE 10

The grading standards of the skin reactions of the patch test

| The skin reactions | Grading Standards |
|---|---|
| No skin reactions | 0 |
| Light erythema | 1 |
| Erythema, infiltration, pimples | 2 |
| Erythema, edema, pimples, blisters | 3 |
| Erythema, edema, bullous | 4 |

Compared with the untested skin, there are no light erythema, swelling and other phenomena on the tested skin after test for 48 hours or 72 hours.

Grading Standards of *camellia* extracts from Example 1 to 11 were 0 according the grading standards of the skin reactions, which says that the *camellia* extract of the present invention has little irritation on skin, and would cause no skin allergies. The *camellia* extract of the present invention has good safety.

EXAMPLE 16

Stability Test

According to stability test method, *camellia* extracts from Example 1 to 11 were stored for 2 months at the following conditions: 50° C. (stored in incubator), 4° C. (stored in refrigerator), at room temperature (25° C., cool and ventilated) or (25° C., direct sunlight). Then observe the color of the *camellia* extracts, and test the DPPH and ABTS radical scavenging rate.

The results show that the color of *camellia* extracts stored at 50° C. for 2 months has slightly lighter, the active ingredients essentially unchanged, the DPPH and ABTS radical scavenging ability remains high. Whether stored at low temperature, room temperature or direct sunlight, the color of *camellia* extracts keeps still, and the active ingredients essentially unchanged. It can be concluded that *camellia* extract of the present invention has good stability.

THE EXAMPLE 17~19

The Preparation of Whitening Toner which Containing the *Camellia* Extract

Formulations of whitening toner which containing the *camellia* extract are in table 11.

TABLE 11

Formulations of whitening toner which containing the *camellia* extract

| Ingredients | | Example 17 | Example 18 | Example 19 |
|---|---|---|---|---|
| | | Weight percentages (%) | | |
| The *camellia* extract | | 2.0 | 5.0 | 10.0 |
| Soothing botanical agents | | 2.0 | 1.0 | 3.0 |
| Polyol moisturizer | Glycerin | 3.0 | 5.0 | 2.0 |
| | 1,3-Butanediol | 4.0 | 2.0 | 6.0 |
| | Trehalose | 5.0 | 2.0 | 0.2 |
| | Betaine | 0.2 | 0.5 | 2.0 |
| *Tremella fuciformis* polysaccharide | | 0.05 | 0.005 | 0.4 |
| Sodium hyaluronate | | 0.01 | 0.2 | 0.005 |
| Phenoxyethanol | | 0.3 | 0.5 | 0.6 |
| Ethylhexylglycerin | | 0.1 | 0.2 | 0.3 |
| Essential oils | | 0.1 | 0.2 | 0.3 |
| water | | The rest is water | The rest is water | The rest is water |

The method to prepare the whitening toner which containing the *camellia* extract is comprised by the following steps:

1) According to the formulation, add water, glycerol, 1,3-butanediol, sodium hyaluronate, Tremella fuciformis polysaccharide, trehalose and betaine into a reactor, then start to stir, and heat until the reaction temperature reaches 75-80° C., keep stirring till stir well;

2) Start the cooling cycle, stir and cool at the same time, and when the reaction temperature reaches 40-45° C., add in the *camellia* extract, botanical soothing agents, phenoxyethanol, ethylhexylglycerin, essential oils, then stir well.

3) Keep stirring, and cooling the whitening emollient water to 38° C., then perform detection, filling, whitening toner is acquired.

THE EXAMPLE 20~22

The Preparation of the Anti-aging Whitening Gel which Containing the *Camellia* Extract Formulations of anti-aging whitening gel which containing the *camellia* extract are in table 12:

TABLE 12

Formulations of anti-aging whitening gel which containing the *camellia* extract

| Ingredients | | Example 20 | Example 21 | Example 22 |
|---|---|---|---|---|
| | | Weight percentages (%) | | |
| The *camellia* extract | | 1.0 | 5.0 | 10.0 |
| Botanical soothing agents | | 1.0 | 2.0 | 3.0 |
| Polyol moisturizer | Glycerin | 4.0 | 6.0 | 2.0 |
| | 1,3-propanediol | 2.0 | 4.0 | 6.0 |
| | Trehalose | 5.0 | 2.0 | 0.2 |
| | Betaine | 1.0 | 0.2 | 2.0 |
| Sodium hyaluronate | | 0.2 | 0.1 | 0.005 |
| Xanthan gum | | 0.5 | 0.9 | 1.0 |
| Disodium EDTA | | 0.05 | 0.1 | 0.20 |
| Phenoxyethanol | | 0.3 | 0.5 | 0.6 |
| Ethylhexylglycerin | | 0.1 | 0.2 | 0.3 |
| Essential oils | | 0.1 | 0.2 | 0.3 |
| water | | The rest is water | The rest is water | The rest is water |

The method to prepare the anti-aging whitening gel which containing the *camellia* extract is comprised by the following steps:

1) According to the formulation, add water, glycerol, 1,3-propanediol, sodium hyaluronate, xanthan gum, disodium EDTA, trehalose and betaine into a reactor, then start to stir, and heat until the reaction temperature reaches 75-80° C., keep stirring till stir well;

2) Start the cooling cycle, stir and cool at the same time, and when the reaction temperature reaches 40-45° C., add in the *camellia* extract, botanical soothing agents, phenoxyethanol, ethylhexylglycerin, and essential oils, then stir well;

3) Keep stirring, and cool the anti-aging whitening gel to 38° C., then perform detection, filling, the anti-aging whitening gel is acquired.

THE EXAMPLE 23~25

The Preparation of the Anti-aging Whitening Lotion which Containing the *Camellia* Extract Formulations of anti-aging whitening lotion which containing the *camellia* extract are in table 13:

TABLE 13

Formulations of anti-aging whitening gel which containing the *camellia* extract

| Ingredients | | Example 23 | Example 24 | Example 25 |
|---|---|---|---|---|
| | | Weight percentages (%) | | |
| The *camellia* extract | | 1.0 | 4.0 | 8.0 |
| Grape seed oil | | 5.0 | 9.0 | 11.0 |
| Olive oil | | 12.0 | 8.0 | 7.0 |
| Polyol moisturizer | Glycerin | 2.0 | 4.0 | 6.0 |
| | 1,3-propanediol | 6.0 | 4.0 | 2.0 |
| Caprylic/capric triglyceride | | 1.5 | 2.5 | 4.0 |
| *Glycine soja* (soybean) seed extract | | 0.5 | 0.8 | 1.0 |
| Carbomer | | 0.5 | 0.2 | 0.8 |
| Sodium hyaluronate | | 0.05 | 0.1 | 0.005 |
| Phenoxyethanol | | 0.3 | 0.5 | 0.6 |
| Ethylhexylglycerin | | 0.1 | 0.2 | 0.3 |
| Sodium hydroxide | | 0.5 | 0.2 | 0.8 |
| Essential oils | | 0.1 | 0.2 | 0.3 |
| water | | The rest is water | The rest is water | The rest is water |

The method to prepare the anti-aging whitening lotion which containing the *camellia* extract is comprised by the following steps:

1) According to the formulation, carbomer and sodium hyaluronate were predispersed by glycerol and 1,3-propanediol, then adding in water and stirring well as A phase alternate.

2) According to the formulation, grape seed oil, olive oil, caprylic/capric triglyceride and *glycine soja* (soybean) seed extract were mixed to form a mixture, then the mixture was added into the A phase alternate which was prepared by step 1) and stir;

3) According to the formulation, sodium hydroxide was added into the A phase alternate which was prepared by step 1), stir well and adjust the stirring speed according to the viscosity;

4) According to the formulation, the *camellia* extract, phenoxyethanol, ethylhexylglycerin, and essential oils were added into A phase alternate, stir well, then perform detection, filling, the anti-aging whitening lotion is acquired.

THE EXAMPLE 26~28

The Preparation of Antioxidant Whitening Sleep Mask which Containing the *Camellia* Extract Formulations of antioxidant whitening sleep mask which containing the *camellia* extract are in table 14:

TABLE 14

Formulations of antioxidant whitening sleep mask which containing the *camellia* extract

| Ingredients | | Example 26 | Example 27 | Example 28 |
|---|---|---|---|---|
| | | Weight percentages (%) | | |
| The *camellia* extract | | 2.0 | 5.0 | 15.0 |
| Polyol moisturizer | Glycerin | 4.0 | 2.5 | 1.0 |
| | 1,3-Propanediol | 4.0 | 2.0 | 6.0 |
| | 1,3-Butanediol | 2.0 | 6.0 | 4.0 |
| Trehalose | | 2.0 | 1.0 | 0.5 |
| *Tremella fuciformis* polysaccharide | | 0.005 | 0.3 | 0.2 |
| Ammonium acryloyldimethyltaurate/VP copolymer | | 0.9 | 0.5 | 0.4 |
| Sodium hyaluronate | | 0.1 | 0.005 | 0.2 |
| Phenoxyethanol | | 0.3 | 0.5 | 0.6 |
| Ethylhexylglycerin | | 0.1 | 0.2 | 0.3 |
| Disodium EDTA | | 0.05 | 0.1 | 0.2 |
| Essential oils | | 0.1 | 0.2 | 0.3 |
| water | | The rest is water | The rest is water | The rest is water |

The method to prepare the antioxidant whitening sleep mask which containing the *camellia* extract is comprised by the following steps:

1) According to the formulation, ammonium acryloyldimethyltaurate/VP copolymer, tremella fuciformis polysaccharide, sodium hyaluronate were predispersed by glycerol, 1,3-propanediol and 1,3-butanediol, then add in water and disodium EDTA, stir well as A phase alternate.

2) According to the formulation, trehalose, the *camellia* extract, phenoxyethanol, ethylhexylglycerin and essential oils were added into the A phase alternate which prepared by step 1), stir well, then perform detection, filling, the antioxidant whitening sleep mask is acquired.

THE EXAMPLE 29-31

The Preparation of the Antioxidant Whitening Cream which Containing the *Camellia* Extract Formulations of antioxidant whitening cream which containing the *camellia* extract are in table 15:

TABLE 15

Formulations of antioxidant whitening cream which containing the *camellia*

| Ingredients | | Example 29 | Example 30 | Example 31 |
|---|---|---|---|---|
| | | Weight percentages (%) | | |
| The *camellia* extract | | 2.0 | 4.0 | 6.0 |
| Jojoba oil | | 5.0 | 8.0 | 12.0 |
| Shea butter | | 8.0 | 6.0 | 4.0 |
| Cetearyl glucoside | | 2.5 | 4.0 | 6.0 |
| Olive oil | | 5.0 | 2.0 | 1.0 |
| Wheat germ oil | | 2.0 | 3.0 | 5.0 |
| Polyol moisturizer | Glycerin | 5.0 | 3.5 | 2.0 |
| | 1,3-Propanediol | 2.0 | 4.0 | 6.0 |
| Caprylic/capric triglyceride | | 1.0 | 3.0 | 5.0 |
| Trehalose | | 4.0 | 2.0 | 0.5 |
| *Glycine soja* (soybean) seed extract | | 1.0 | 0.5 | 0.2 |
| Vitamin E acetate | | 0.5 | 0.2 | 0.05 |
| *Tremella fuciformis* polysaccharide | | 0.2 | 0.005 | 0.1 |
| Sodium hyaluronate | | 0.005 | 0.1 | 0.05 |
| Phenoxyethanol | | 0.3 | 0.5 | 0.6 |
| Ethylhexylglycerin | | 0.1 | 0.2 | 0.3 |

TABLE 15-continued

Formulations of antioxidant whitening
cream which containing the camellia

| Ingredients | Example 29 | Example 30 | Example 31 |
|---|---|---|---|
| | Weight percentages (%) | | |
| Essential oils | 0.1 | 0.2 | 0.3 |
| water | The rest is water | The rest is water | The rest is water |

The method to prepare the antioxidant whitening cream which containing the camellia extract is comprised by the following steps:

1) According to the formulation, tremella fuciformis polysaccharide and sodium hyaluronate were predispersed by glycerol and 1,3-propanediol, adding in water and trehalose, heating until the reaction temperature reaches 75° C., and stir well as the aqueous phase alternate.

2) According to the formulation, jojoba oil, shea butter, Cetearyl glucoside, olive oil, wheat germ oil, Caprylic/capric triglyceride, Glycine soja (soybean) seed extract and vitamin E acetate were mixed, heat until the reaction temperature reaches 75° C., stir well as the oil phase alternate.

3) The oil phase alternate prepared by step 2) was added into the aqueous phase alternate prepared by step 1), stir well to form a mixture, and then letting the mixture homogeneous for 3 minutes.

4) Stirring and cooling at the same time until the temperature of the mixture falls down to 35° C.~40° C., then add in the camellia extract, phenoxyethanol, ethylhexylglycerin, and essential oils, stir well, then perform detection, filling, the antioxidant whitening cream is acquired.

EXAMPLE 32

Performance Evaluation of Skin Care Products

Skin evaluation instrument from the Courage+Khazaka electronic GmbH (CK) was adopted to test the skin wrinkles and skin appearance after using skin care products prepared by Example 15-20.

(I), Skin Appearance Test

Figure 5:
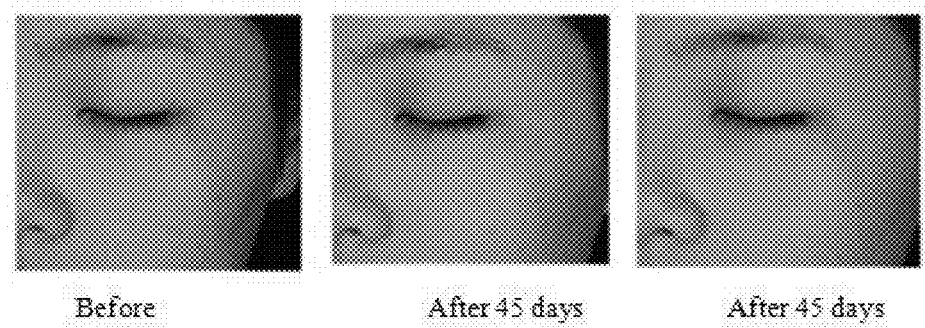
FIG. 5 is a comparison graphic of the skin appearance before and after using cosmetics that containing the *camellia* extract.
Figure 6:
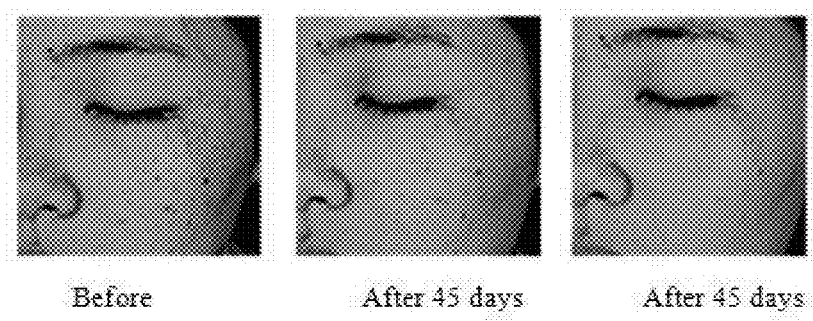
FIG. 6 is a comparison graphic of the skin condition by infrared shooting before and after using cosmetics that containing the *camellia* extract.

The process of skin care involves multiple steps, generally including: washing face, slapping on toner, lotion, gel, cream, and using sleep mask. Therefore, it needs to use all the skin care products prepared by Example 17 to 31 mentioned above. Now, skin appearance before and after skin care by the products containing the camellia extract is detected. Participant who uses the skin care products was taken pictures and infrared shooting before the test, on 45 days and 90 days respectively, and the test results are shown in FIG. 5 and FIG. 6, It can be seen from FIG. 5 and FIG. 6 that before using the skin care products, participant has many skin spots on the face, and with dull skin and uneven skin tone; after using the skin care products a period of time, the pigmented skin layer becomes uniform and the skin spots are significantly reduced, and the skin becomes symmetry.

It can be concluded that the camellia extract is a cosmetic active ingredient in the skin care product, the skin care product containing the camellia extract as active ingredient has an excellent whitening, spot-fading effect.

(II), Skin Wrinkles Test

Figure 7:
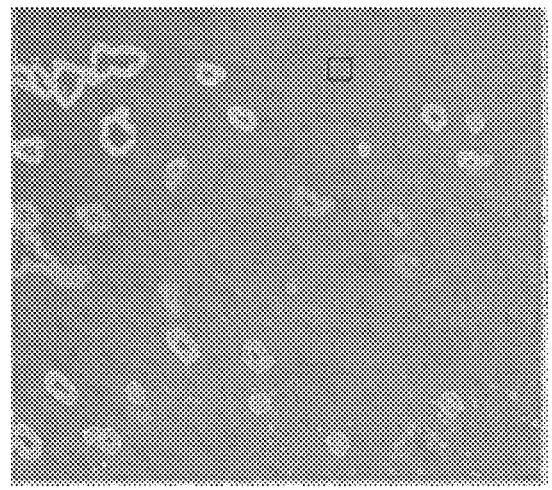
FIG. 7 is a graphic of the skin wrinkles before using cosmetics that containing the *camellia* extract.
Figure 8:
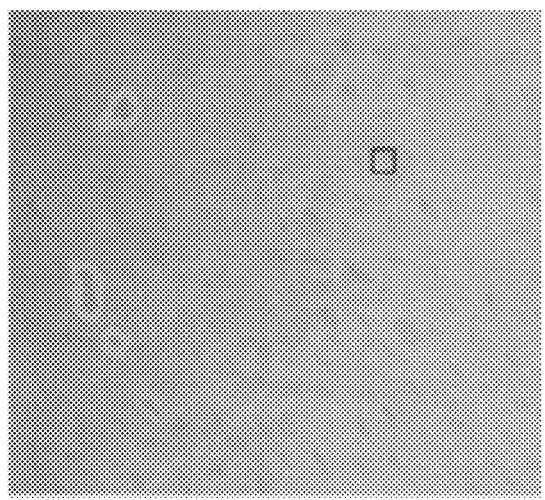
FIG. 8 is a graphic of the skin wrinkles after using cosmetics that containing the *camellia* extract.

Infrared shot was used on the local skin for the skin wrinkles test, the test results are shown in FIG. 7 and FIG. 8, and wherein the white circle represents wrinkles. By a comparison of FIGS. 7 and 8, it can be seen that the skin wrinkles were significantly reduced after using the skin care products that containing the camellia extract. From the analysis of the infrared shot instrument, the test area ratio of skin wrinkles is 3.362% before using the skin care products, after using the skin care products for a period of time, the test area ratio of skin wrinkles falls down to 1.430%. It says that the skin care product which containing the camellia extract have a good anti-aging, anti-wrinkle effect.

Whether use alone or use together with other cosmetic products, the skin care products of the present invention described above have the same whitening, spot-fading, anti-aging effect.

Specific embodiments of the present invention have been described in detail above, but they are just as examples rather than limiting its scope. For the technical personnel in this field, any equivalent modifications or substitutions of the invention should be included within the scope of the invention. Thus, equivalent changes and modifications without departing from the spirit and the scope of the present invention should be included within the scope of the present invention.

The invention claimed is:

1. A method for making a Camellia extract, comprising the following steps:
   1) removing impurities from fresh Camellia and/or fresh Camellia buds;
   2) cutting the fresh Camellia and/or fresh Camellia buds into pieces for use as raw materials;
   3) placing the raw materials into an ultrasonic vessel,
   4) adding in a solvent having a mass ratio to the raw materials of 1:3 to 1:30 to form a mixture;
   5) uniformly stirring the mixture; and then
   6) adding an inorganic acid and/or organic acid to adjust the pH value to 1.3 to 3.0: then
   7) soaking the raw materials for 10 minutes to 30 minutes;
   8 treating the composition made in step 7 with ultrasound for 30 minutes to 60 minutes, wherein the ultrasonic frequency is 20 KHz to 25 KHz, the ultrasonic power is 1000 W to 2000 W, and the temperature is 15° C. to 50° C.;
   9) filtering the composition made in step (8); and
   10) sterilizing the filtrate obtained in step (9), to obtain a Camellia extract.

2. The method as claimed in claim 1, wherein the length of the pieces in step 1) is 0.5 cm to 3 cm.

3. The method as claimed in claim 1, wherein the mass ratio between the acid and the solvent in step 6) is 0.25% to 2.5%, wherein the acid is an inorganic acid, an organic acid, or a mixture thereof.

4. The method as claimed in claim 1, wherein the solvent in step 4) is water, ethanol, 1,3-propanediol, 1,2-propanediol, glycerin, 1,3-butanediol, sorbitol, or a mixture thereof.

5. The method as claimed in claim 1, wherein the inorganic acid in step 6) is hydrochloric acid.

6. The method as claimed in claim 1, wherein the organic acid in step 6) is phytic acid, citric acid, ascorbic acid, lactic acid, acetic acid or a mixture thereof.

7. The Camellia extract prepared by the method of claim 1.

8. The Camellia extract of claim 7, wherein the Camellia extract contains antioxidant ingredients as follows: kaempferol: 0.43-4.52 ppm, quercetin: 1.09-8.17 ppm, and quercitrin: 45.62-197.81 ppm.

9. A whitening toner containing the Camellia extract of claim 7, wherein the Camellia extract is an active ingredient, and wherein the whitening toner comprises, by weight:

*Camellia* extracts 2.0-10.0%, botanical soothing agent 1.0%-3.0%, glycerin 2.0% -5.0%, 1,3-butanediol 2.0%-6.0%, trehalose 0.2%-5.0%, betaine 0.2% -2.0%. *Tremella fuciformis* polysaccharide 0.005%-0.4%, sodium hyaluronate 0.005%-0.2%, phenoxyethanol 0.3%, -0.6%, ethylhexylglycerin 0.1%-0.3%, and essential oils 0.1-0.3%, wherein the remainder is water.

10. An anti-aging whitening gel containing the *Camellia* extract of claim 7, wherein the *Camellia* extract is an active ingredients, and wherein the anti-aging whitening gel comprises, by weight: *Camellia* extract 1.0%-10.0%, botanical soothing agent 1.0%-3.0%, glycerin 2.0% -6.0%, 1,3-propanediol 2.0%-6.0%, trehalose 0.2%-5.0%, betaine 0.2%-2.0% sodium hyaluronate 0.005%-0.2% xanthan gum 0.5%-1.0%, disodium EDTA 0.05% -0.20%, phenoxyethanol 0.3%-0.6%, ethylhexylglycerin 0.1%-0.3%, and essential oils 0.1% -0.3%, wherein the remainder is water.

11. An anti-aging whitening lotion containing the *Camellia* extract of claim 7, wherein the *Camellia* extract is an active ingredient, and wherein the anti-aging whitening lotion comprises, by weight: *Camellia extract* 1.0%-8.0%, grape seed oil 5.0%-11%, olive oil 7.0% to 12%, glycerin 2.0%-6.0%, 1,3-propanediol 2.0% 6.0%, caprylic/capric triglyceride 1.5%-4.0%. Glycine soja seed (soybean) extract 0.5%-1.0%, carbomer 0.2%-0.8%, sodium hyaluronate 0.005%-0.1%, phenoxyethanol 0.3%-0.6%, ethylhexylglycerin 0.1%-0.3%, essential oils 0.1%-0.3% and sodium hydroxide (as a 33% by weight solution) 0.2% -0.8%, wherein the remainder is water.

12. An antioxidant whitening sleep mask containing the *Camellia* extract of claim 7, wherein the *Camellia* extract is an active ingredient, and wherein the antioxidant whitening sleep make comprises, by weight: *Camellia* extract 2.0%-15.0%, glycerin 1.0% -4.0% 1,3-propanediol 2.0%-6.0%, 1,3-butanediol 2.0%-6.0%, trehalose 0.5%-2.0%, *Tremelia fuciformis* polysaccharide 0.005%-0.3%, ammonium acryloyldimethyltaurate/VP copolymer 0.4% 0.9%, sodium hyaluronate 0.005%-0.2% disodium EDTA 0.05%-0.2%, phenoxyethanol 0.3%-0.6%, ethylhexylglycerin 0.1%-0.3%, and essential oils 0.1% -0.3%, wherein the remainder is water.

13. An antioxidant whitening cream containing the *Camellia* extract of claim 7, wherein the *Camellia* extract is an active ingredient, and wherein the antioxidant whitening cream comprises, by weight: *Camellia* extract 2.0%-6.0%, jojoba oil 5.0%-12%, shea butter 4.0% to 8%, cetearyl glucoside 2.5%-6.0%, olive oil 1.0%-5.0%, wheat germ oil 2.0%-5.0%, glycerin 2.0%-5.0%, 1,3-propanediol 2.0%-6.0%, caprylic/capric triglyceride 1.0%-5.0%, trehalose 0.5%-4.0%, Glycine soja seed (soybean) extract 0.5%-1.0%, tocopheryl acetate 0.05%-5%, sodium hyaluronate 0.005%-0.1%, *Tremella fuciformis* polysaccharide 0.005%-0.2%, phenoxyethanol 0.3%-0.6%, ethylhexylglycerin 0.1%-0.3%, essential oils 0.1%-0.3% and essential oils 0.1%-0.3%, wherein the remainder is water.

\* \* \* \* \*